United States Patent [19]

Yoshioka et al.

[11] Patent Number: 5,225,062

[45] Date of Patent: Jul. 6, 1993

[54] ELECTROPHORETIC GEL FOR SEPARATION AND RECOVERY OF SUBSTANCES AND ITS USE

[75] Inventors: Hiroshi Yoshioka; Yuichi Mori, both of Kanagawa, Japan

[73] Assignee: W. R. Grace & Co. -Conn., New York, N.Y.

[21] Appl. No.: 826,725

[22] Filed: Jan. 28, 1992

[30] Foreign Application Priority Data

Feb. 27, 1991 [JP] Japan ................... 3-32643
Feb. 27, 1991 [JP] Japan ................... 3-32644

[51] Int. Cl.⁵ .................... G01N 27/26; G01N 27/447
[52] U.S. Cl. ............................. 204/299 R; 204/182.8
[58] Field of Search ........................ 204/299 R, 182.8

[56] References Cited

U.S. PATENT DOCUMENTS

| | | | |
|---|---|---|---|
| 4,504,569 | 3/1985 | Abel et al. | 430/216 X |
| 4,780,409 | 10/1988 | Monji et al. | 435/7.36 |
| 4,828,701 | 5/1989 | Cussler | 210/774 X |
| 4,863,613 | 9/1989 | Johnson et al. | 210/774 X |
| 4,900,416 | 2/1990 | Makino | 204/299 R |
| 4,912,032 | 3/1990 | Hoffman et al. | 435/6 X |
| 5,053,228 | 10/1991 | Mori et al. | 424/486 |
| 5,057,560 | 10/1991 | Mueller | 524/521 X |

FOREIGN PATENT DOCUMENTS 0115436 8/1984 European Pat. Off. .
0119808 9/1984 European Pat. Off. .
WO88/09981 12/1988 PCT Int'l Appl. .
WO91/14489 10/1991 PCT Int'l Appl. .

OTHER PUBLICATIONS

Allan S. Hoffman et al. "Thermally Reversible Hydrogels: 11. Delivery and Selective Removal of Substances from Aqueous Solutions" Journal of Controlled Release 4 (1986) 213-222.

*Primary Examiner*—John Niebling
*Assistant Examiner*—John S. Starsiak, Jr.
*Attorney, Agent, or Firm*—Beverly K. Johnson

[57] ABSTRACT

An electrophoretic gel comprising at least one crosslinked temperature-responsive polymeric compound having an LCST is disclosed. A method of separating and recovering substances involves conducting the electrophoresis of a sample containing substances to be separated using the electrophoretic gel at a temperature below the LCST, excising each portion of the gel containing the substance to be separated and raising the temperature of the excised portion to a temperature above the LCST to shrink the excised portion to recover the substances.

6 Claims, No Drawings

ELECTROPHORETIC GEL FOR SEPARATION AND RECOVERY OF SUBSTANCES AND ITS USE

FIELD OF INVENTION

The present invention relates to an electrophoretic gel for the separation and recovery of substances. More particularly, it relates to an electrophoretic gel made of at least one crosslinked temperature-responsive polymeric substance having an LCST. The present invention also relates to a method of separating and recovering substances by using the electrophoretic gel.

BACKGROUND OF THE INVENTION

Various methods for the separation and recovery of proteins, nucleic acids or their fragments are carried out by electrophoresis for the preparation of recombinant DNA, the cloning of DNA, the preparation of antibodies, the determination of amino acid sequences, the mapping of peptides and the analysis of amino acids. For instance, a method of electrical elution which comprises excising the gel containing the substances separated by electrophoresis and re-exposing the gel thus excised to an electrical field to elute the substances from the gel, a blotching method which comprises superimposing a filter paper or a nitrocellulose film on the gel containing the substances to be separated to transfer them to the carrier, a gel structuring method which comprises crushing and pulverizing to extract the substances to be separated, and a gel dissolution method which comprises decomposing the crosslinks of the gel by a chemical reaction to elute off the substances in the gel, having been developed. However, these methods have been said to be disadvantageous in that numerous complicated recovery steps are required, the recovery rate is low and the sample is denatured. Particularly fatal is the low recovery rate when such methods are used to separate and recover trace amounts of proteins or nucleic acids.

On the other hand, solubilizable gels have been developed for the purpose of achieving a high recovery yield. When N,N'-methylenebisacrylamide is employed as the conventional crosslinking agent, the polyacrylamide gel thus obtained has to be solubilized under a comparatively severe condition as in an aqueous 30% (w/v) hydrogen peroxide solution at 50° C. However, the solubilizable gels can be dissolved in an aqueous solution under a comparatively mild condition. Typical gels are ones which can be obtained by crosslinking the polyacrylamides with a decomposable crosslinking agent such as N,N'-diallyltartardiamide, N,N'-(1,2-dihydroxyethylene)bisacrylamide, N,N'-bisacrylcystamine and ethylene diacrylate. A method which comprises separating substances by electrophoresis using the above described gel, excising each portion containing said substances, respectively, and solubilizing the excised portions of the gel by oxidation, reduction or hydrolysis to elute the substances in the gel, has been developed. However, the problem with this method is that the separated proteins or nucleic acids have to be re-separated from the solubilized gel. Particularly at the time when the gel is solubilized, even if 100% recovery yield is possible, the yield of recovery may be disadvantageously decreased in the later step of the separation from the solubilized gel [for example, see D. C. Flter and S. S. Tevethia: Virology, 117:267-270 (1982)].

Thus, even when the conventional method is employed for the separation of substances by electrophoresis, it is very difficult to recover the substances from the gel by a simple method and at a high recovery yield.

OBJECTS

An object of this invention is to provide a novel electrophoretic gel for the separation and recovery of substances which avoids the above described problems associated with the conventional electrophoretic methods.

Another object of this invention is to provide a novel method for the separation and recovery of desired substances such as proteins and nucleic acids at a high recovery yield which method employs such an electrophoretic gel.

DEFINITION

The term "LCST" is used herein to mean a lower critical solution temperature which is a transition temperature of a temperature-responsive polymeric compound between hydration and dehydration.

SUMMARY OF THE INVENTION

The electrophoretic gel for the separation and recovery of substances in accordance with the present invention comprises at least one crosslinked temperatureresponsive polymeric compound having an LCST.

In another aspect of the invention, the electrophoretic gel for the separation and recovery of substances comprises at least one decomposable crosslinked temperature-responsive polymeric compound having an LCST.

In a further aspect of the invention, a method of separating and recovering substances comprises the steps of:

(a) conducting electrophoresis of a sample containing substances to be separated using an electrophoretic gel for the separation and recovery of substances which gel is made of at least one crosslinked temperature-responsive polymeric compound having an LCST at a temperature below said LCST;

(b) excising or removing each portion of the gel containing the substance to be separated;

(c) shrinking the excised portion of the gel by raising the temperature of the excised portion to a temperature above the LCST of said gel to recover said substances.

In a still further aspect of the invention a method of separating and recovering substances comprises the steps of:

(a) conducting electrophoresis of a sample containing substances to be separated using an electrophoretic gel for the separation and recovery of substances which gel is made of at least one decomposable crosslinked temperature-responsive polymeric compound having an LCST at a temperature below said LCST;

(b) excising each portion of the gel containing the substance to be separated;

(c) decomposing the crosslinks in said gel by oxidation, reduction or hydrolysis;

(d) precipitating the decomposed temperature-responsive polymeric compound by raising the temperature of said gel to a temperature above the LCST of the gel; and (e) removing the temperature-responsive polymeric compound thus precipitated to recover said substances.

DETAILED EXPLANATION OF THE INVENTION

The electrophoretic gel for the separation and recovery of substances in the present invention employs at least one crosslinked temperature-responsive polymeric compound.

The crosslinked temperature-responsive polymeric compound may also be decomposable by oxidation, reduction or hydrolysis.

A temperature-responsive polymeric compound shows, in the presence of water, hydrophobicity at a temperature higher than the LCST and changes to show hydrophilicity at a temperature below the LCST, and such a change is characterized by being thermally reversible.

Change of state of the temperature-responsive polymer compounds is said to be caused by hydration and dehydration. This has been explained by Haskins, M., et al. in *J. Macromol. Sci. Chem.*, A2 (8), 1441, 1968, using as the sample the poly(N-isopropylacrylamide) (hereinafter "PNIPAAm") which is one of such polymeric compounds. PNIPAAm is a polymeric compound which has a negative temperature coefficient of solubility. PNIPAAm shows hydrophilic property at a lower temperature because a hydrate, i.e. oxonium hydroxide, which depends on the hydrogen bond of PNIPAAm molecule and water molecule is formed at low temperatures. However, because the oxonium hydroxide degrades and dehydrates when temperature is raised above the LCST, the PNIPAAm molecule becomes hydrophobic and aggregates and precipitates as a result.

In the present invention it is preferred to use a temperature-responsive polymeric compound having its LCST at 0° C. to 90° C., preferably at 10° C. to 50° C.

The temperature-responsive polymeric compound which can be used in the present invention is insoluble in water and remains in a solid state at a temperature above the LCST, and it becomes soluble in water in a reversible manner when temperature is lowered to a temperature below the LCST.

Examples of such temperature-responsive polymeric compounds include poly-N-substituted acrylamide or methacrylamide derivatives and their copolymers, polyvinylmethyl ether, polyethyleneoxide, etherized methylcellulose, and partially acetylated polyvinyl alcohol. Particularly preferred are poly-N-substituted methacrylamide or acrylamide derivatives and their copolymers, polyvinylmethyl ether, and partially acetylated polyvinyl alcohol.

Preferred examples of such temperature-responsive polymeric compounds are listed below. The LCSTs of these polymers rise with the sequence of polymers listed below.

Poly(N-acryloyl piperidine);
Poly(N-n-propyl- methacrylamide);
Poly(N-isopropyl acrylamide);
Poly(N,N-diethyl acrylamide);
Poly(N-isopropyl methacrylamide);
Poly(N-cyclopropyl acrylamide);
Poly(N-acryloyl pyrrolidine);
Poly(N,N-ethylmethyl acrylamide);
Poly(N-cyclopropyl methacrylamide);
Poly(N-ethyl acrylamide).

The above described polymers may be homopolymers or copolymers with other monomers. Any hydrophilic monomers and hydrophobic monomers can be used as the monomers for copolymerization. Generally speaking, copolymerization with a hydrophilic monomer will raise the LCST, and copolymerization with a hydrophobic monomer will lower the LCST. With an appropriate selection of the monomers, a copolymer having a desired LCST can be obtained.

Examples of suitable hydrophilic monomers are N-vinyl-pyrrolidone, vinylpyridine, acrylamide, methacrylamide, N-methyl acrylamide, hydroxyethyl methacrylate, hydroxyethyl acrylate, hydroxymethyl methacrylate, hydroxymethyl acrylate, acrylic acid and methacrylic acid and their salts, vinylsulfonic acid and styrylsulfonic acid and their salts, vinylsulfonic acid, styrylsulfonic acid, and N,N-dimethylaminoethyl methacrylate, N,N-diethylaminoethyl methacrylate, and N,N-dimethylaminopropyl acrylamide and their salts, but the present invention is not limited to these compounds.

Examples of suitable hydrophobic monomers are acrylate or methacrylate derivatives such as ethyl acrylate, methyl methacrylate and glycidyl methacrylate; N-substituted alkyl acrylamide or methacrylamide derivatives such as N-n-butyl acrylamide or methacrylamide; vinyl chloride; acrylonitrile; styrene; and vinyl acetate but the present invention is not limited to these compounds.

The crosslinked temperature-responsive polymeric compound which can be used as the electrophoretic gel in the present invention can be prepared by copolymerizing a bifunctional monomer with the monomer capable of giving the above described temperature-responsive polymer. Suitable examples of such bifunctional monomers include N,N'-methylenebisacrylamide, N,N'-methylenebismethacrylamide, allyl acrylate or methacrylate, ethylene glycol diacrylate or dimethacrylate, diethylene glycol diacrylate or dimethacrylate, triethylene glycol diacrylate or dimethacrylate, propylene glycol diacrylate or dimethacrylate, divinylbenzene, divinyl ether and bisphenol A diacrylate or dimethacrylate.

Also, according to the present invention the crosslinked temperature-responsive polymeric compound which can be employed as the electrophoretic gel may be decomposable. Such decomposable crosslinked temperature-responsive polymeric compounds can be prepared by copolymerizing a bifunctional monomer having a decomposable linkage.

The term "decomposable" is used herein to mean that the crosslinks formed in the gel can be decomposed with a minimum damage to the substances to be separated and recovered, such as proteins and nucleic acids, by oxidation, reduction or hydrolysis. The decomposable linkages include a disulfide linkage, an ester linkage and an aminomethylol linkage. Suitable examples of such bifunctional monomers having a decomposable linkage which can be employed in the present invention includes N,N'-diallyltartardiamide, N,N'-(1,2-dihydroxyethylene)bisacrylamide, N,N'-bisacrylcystamine, and ethylene diacrylate.

The amount of the above described bifunctional monomer of two types which can be copolymerized with the monomer capable of giving the temperature-responsive polymer is typically about 0.005 to about 5% by weight, preferably about 0.1 to about 1% by weight based of the weight of the temperature-responsive polymeric compound. When the amount of the bifunctional monomer is less than 0.005% by weight based on the weight of the temperature-responsive polymeric compound, the mechanical strength of the gel is not sufficient and the separation yield decreases. On the other hand, amounts of more than 5% by weight based on the weight of the temperature-responsive polymeric compound decrease the degree of change in shrinking and swelling depending on the temperature of the gel to reduce the recovery yield of the substances. The gel of the present invention can be prepared by hydrating the copolymer after carrying out the bulk copolymerization of the monomer capable of giving a temperature-responsive polymeric compound with or without the above described hydrophilic monomer or hydrophobic monomer and the bifunctional monomer, or by the copolymerization of these monomers in water, preferably at a constant temperature below the LCST of the temperature-responsive polymeric compound, as used to obtain the conventional acrylamide gels used for electrophoresis. The latter method is preferred since the gel obtained as such can be provided with the electrophoresis. Although there is no particular restriction on the type of polymerization method to be used herein, it is preferred to conduct the radical polymerization in water at low temperatures using a redox initiator system such as a combination of ammonium persulfate and N,N,N'N'-tetramethylenediamine.

The method of separating and recovering proteins or nucleic acids by using the gel as obtained above will now be explained. First, the proteins or nucleic acids are separated by the electrophoresis using the gel of the present invention. It is essential that the electrophoresis is carried out at a temperature below the LCST of the crosslinked temperature-responsive polymer forming the gel, but the other procedures equivalent to the conventional slab electrophoresis can be used. Second, each portion of the gel containing the substance separated by the electrophoresis is excised from the gel. Third, the excised portion of the gel is shrunk by raising the temperature of the gel to a temperature above the LCST of the gel to recover the substance. It is also possible to successively repeat the procedure of swelling the excised portion of the gel by lowering the temperature of the gel to a temperature below the LCST of the gel and the procedure of shrinking the excised portion of the gel by raising the temperature of the gel to a temperature above the LCST of the gel at least twice to recover the substance at a higher recovery yield.

When the decomposable crosslinked temperature-responsive polymeric compound is employed for the gel of the present invention, the method as shown below can be additionally employed.

First, the separation of proteins or nucleic acids is carried out by the electrophoresis using the gel made of at least one decomposable crosslinked temperatureresponsive polymeric compound at a temperature below the LCST of the polymeric compound. Second, each portion of the gel containing the substance separated by the electrophoresis is excised. Third, the crosslinks in each portion of the gel is decomposed by oxidation, reduction or hydrolysis, preferably at a temperature below LCST of the decomposable crosslinked temperature-responsive polymeric compound, to solubilize the gel in an aqueous solution. In this instance, when N,N'-bisacrylcystamine is employed as the bifunctional monomer, 2-mercaptoethanol is typically employed for the decomposition of the crosslinks in the gel by reduction. When N, N'-diallyltartardiamide or N,N'-(1,2-dihydroxyethylene)bisacrylamide is employed as the bifunctional monomer, periodic acid is typically employed for the decomposition of the crosslinks in the gel by oxidation. When ethylene diacrylate is employed as the bifunctional monomer, an alkali is typically employed for the decomposition of the crosslinks in the gel by hydrolysis. However, any other reactions which will not denature the substances to be separated can also be used to decompose the crosslinks in the gel. Fourth, the temperature of the aqueous solution containing the solubilized gel and the substance to be separated is raised to a temperature above the LCST of the decomposable crosslinked temperature-responsive polymeric compound to precipitate the decomposed temperature-responsive polymeric compound. Then, by removing the precipitated temperature-responsive polymeric compound the desired substance can be obtained at a high yield. A centrifugation method or a membrane filtration method can be used for the removal of the precipitated temperature-responsive polymeric compound whose crosslinks have been decomposed. However, any other separation method can be used as long as they can recover the substance without its denaturation.

The present invention is further explained by the following examples which are given for illustrative purposes and are not meant to limit the invention.

EXAMPLE I

A micro slab electrophoretic device (KS-8012, a product of Marisol Co. in Japan) was used for the prepration of a gel for the electrophoresis and for the electrophoresis of proteins. N-Isopropylacrylamide 1.5 g and N,N'-methylene bisacrylamide 0.0102 g were dissolved in 10 ml of a 0.375 M Tris-Cl buffer solution (pH 8.8) and deaerated for 10 minutes by means of a water aspirator. Then, an aqueous 10% (w/v) ammonium persulfate solution 0.033 ml and N,N,N',N'-tetramethylenediamine 0.0033 ml were added to the solution and the resulting solution was poured into a space having a width of 8.5 cm and a height of 7 cm between two glass plates having a 1 mm spacer and a comb was inserted into the space. The assembly thus prepared was left to stand overnight in a thermostat at 20° C. in a nitrogen atmosphere to gel the solution.

The gel thus obtained was fixed in the electrophoretic device and both the cathode and anode chambers were filled with a 0.025M Tris-0.192M glycine buffer solution having a pH of 8.4. As sample proteins bovine hemoglobin having a molecular weight of 65,000 (hereafter "Hb") and horse heart myoglobin having a molecular weight of 18,800 (hereafter "Mb") were used. 0.01 ml of a 1 weight % solution of each protein was poured onto each well and electrophoresis was conducted for 40 minutes by applying a constant current of 20 mA to the gel. During the electrophoresis the temperature of the gel was kept at 20° C., i.e., a temperature lower than 30° C. which is the LCST of poly(N-isopropylacrylamide). Hb having a greater molecular weight than Mb showed a smaller mobility in the gel due to the molecular sieving effect. After the electrophoresis colored portions of the swollen gel (about 0.2 g) were excised, finely crushed and precisely weighed. After 0.1 ml of a 67 mM phosphate buffer solution was added to the crushed gel, the gel three times alternatingly underwent shrinking at 37° C., i.e., a temperature higher than the LCST of poly(N-isopropylacrylamide) and swelling at 4° C., i.e., a temperature lower than the LCST of poly(N-isopropylacrylamide) and finally by shrinking the gel at 37° C., an aqueous solution discharged was collected and the amount of Hb or Mb in the solution was quantitatively analyzed by a protein assay kit (a product of Bio Rad Co., U.S.A.). As a result, it was confirmed that almost all the proteins employed in the electrophoresis were recovered.

EXAMPLE II

The procedures of Example I for obtaining the finely crushed gel were repeated except that N,N'-bisacrylcystamine 0.0102 g was employed instead of N,N'-methylenebisacrylamide.

Then, 2 ml of a 67 mM phosphorate buffer solution containing 10% by weight of 2-mercaptoethanol were added to the crushed gel and stirred at 20° C. for 30 minutes to dissolve the gel. The temperature of the solution thus obtained was raised to 37° C., i.e., a temperature higher than the LCST of poly(N-isopropylacrylamide) to precipitate the decomposed temperature-responsive polymeric compound and the polymeric compound was centrifuged at 37° C. for 10 minutes (10,000 G). The amount of Hb or Mb in the supernatant liquid was quantitatively analyzed by a protein assay kit (a product of Bio Rad Co. in U.S.A.). As a result, almost all the proteins employed in the electrophoresis were recovered.

EXAMPLE III

The procedures of Example II were repeated except that N,N'-diallyltartardiamine 1.0102 was employed instead of the N,N'-bisacrylcystamine 0.0102 g and 2 ml of 2% by weight of periodic acid were employed instead of the 2 ml of a 67 mM phosphate buffer solution containing 10% by weight of 2-mercaptoethanol.

As a result, almost all the proteins employed in the electrophoresis were recovered.

As would easily be understood from the above description of the invention, the desired substances, especially proteins and nucleic acids, can easily and simply be recovered without any denaturation of the substances at a high recovery yield by using the electrophoretic gel of the present invention.

We claim:

1. An electrophoretic gel for the separation and recovery of substances comprising at least one crosslinked temperature-responsive polymeric compound having an LCST which is ia copolymer decomposable by oxidation or reduction, said copolymer being made of a monomer capable of giving a temperature-responsive polymeric compound selected from the group consisting of N-acryloyl piperidine, N-n-propyl methacrylamide, N-isopropyl acrylamide, N,N-diethyl acrylamide, N-isopropyl methacrylamide, N-cyclopropyl acrylamide, N-acryloyl pyrrolidine, N,N-ethylmethyl acrylamide, N-cyclopropyl methacrylamide and N-ethyl acrylamide and a bifunctional monomer selected from the group consisting of N,N'-diallyltartardiamide, N,N'-(1,2-dihydroxyethylene)-bisacrylamide and N,N'-bisacrylcystamine.

2. The gel of claim 1, wherein the amount of said bifunctional monomer is 0.005 to 5% by weight based on the weight of said crosslinked temperature-responsive polymeric compound.

3. The gel of claim 1, wherein said monomer is N-isopropyl acrylamide.

4. The gel of claim 1, wherein said bifunctional monomer is N,N'-diallyltartardiamide.

5. The gel of claim 1, wherein said bifunctional monomer is N,N'-biacrylcystamine.

6. The gel of claim 1, wherein said copolymer is made of said monomer capable of giving a temperature-responsive polymeric compound, said bifunctional monomer, and a hydrophilic monomer or a hydrophobic monomer.

* * * * *